US007696371B2

United States Patent
Davis et al.

(10) Patent No.: US 7,696,371 B2
(45) Date of Patent: Apr. 13, 2010

(54) METHOD FOR THE PREPRATION OF ALIPHATIC CHLOROFORMATES

(75) Inventors: Gary Charles Davis, Albany, NY (US); Joshua James Stone, Clifton Park, NY (US); James Manio Silva, Clifton Park, NY (US); James Alan Mahood, Evansville, IN (US); David Michel Dardaris, Ballston Spa, NY (US)

(73) Assignee: SABIC Innovative Plastics IP B.V., Bergen op Zoom (NL)

( * ) Notice: Subject to any disclaimer, the term of this patent is extended or adjusted under 35 U.S.C. 154(b) by 1281 days.

(21) Appl. No.: 10/968,773

(22) Filed: Oct. 19, 2004

(65) Prior Publication Data

US 2006/0084822 A1    Apr. 20, 2006

(51) Int. Cl.
*C07C 69/96*    (2006.01)
(52) U.S. Cl. ...................................... 558/280; 558/282
(58) Field of Classification Search ........................ None
See application file for complete search history.

(56) References Cited

U.S. PATENT DOCUMENTS 6,696,590 B2 *    2/2004    Bonnard et al. ............. 558/280

FOREIGN PATENT DOCUMENTS

| CS | 190 921 | 9/1978 | |
|---|---|---|---|
| GB | 1 379 977 | * | 1/1975 |
| JP | 48043489 | | 12/1973 |
| JP | 48043490 | | 12/1973 |
| JP | 51 41328 | | 10/1974 |

OTHER PUBLICATIONS

Witold Missner & Ryszard Zielinski, "Method of Prepartation of Alkyl Chloroforamtes", 1978, Zeszyty Naukowe—Akademia Ekonomiczna w Poznaniu, Seria 1: Prace z Zakresu Towaroznawstwa i Chemii, vol. 73, pp. 92-96, Coden: Znasdh; ISSN: 0208-4902.

* cited by examiner

*Primary Examiner*—Daniel M Sullivan
*Assistant Examiner*—Sudhakar Katakam

(57) ABSTRACT

A method for preparing an aliphatic chloroformate comprising, introducing a mixture of at least one aliphatic hydroxyl compound, phosgene, at least one solvent, and optionally at least one organic base into a flow reactor to obtain a unidirectional flowing reaction mixture. The at least one aliphatic hydroxyl compound comprises at least one aliphatic hydroxyl group. The unidirectional flowing reaction mixture is maintained at a temperature between about 0° C. and about 60° C. to produce a single product stream comprising an aliphatic chloroformate.

19 Claims, No Drawings

METHOD FOR THE PREPRATION OF ALIPHATIC CHLOROFORMATES

BACKGROUND OF THE INVENTION

This invention relates to a method for preparing an aliphatic chloroformate useful in the preparation of polycarbonates and co-polycarbonates. More particularly the method relates to a method for preparing an aliphatic chloroformate in a flow reactor.

Aliphatic alcohols may be phosgenated in both batch processes and continuous processes to provide aliphatic chloroformates. Despite extensive research and development efforts concentrated towards the more efficient manufacture of aliphatic chloroformates, deficiencies in the manufacture of chloroformates remain.

It is of interest therefore, to develop new and more efficient processes for the formation of aliphatic chloroformates that overcome the limitations of known methods, and which achieve increased ease of operation and economic feasibility, while providing aliphatic chloroformates of high purity in high yield.

BRIEF SUMMARY OF THE INVENTION

The present invention provides a method for the preparation of aliphatic chloroformates. The method comprises introducing a mixture of at least one aliphatic hydroxyl compound, phosgene, at least one solvent, and optionally at least one organic base into a flow reactor to obtain a unidirectional flowing reaction mixture. The unidirectional flowing reaction mixture inside the flow reactor is maintained at a temperature between about 0° C. and about 60° C. to produce a product stream comprising an aliphatic chloroformate.

In another aspect the present invention provides a method for preparing a co-polycarbonate. The method comprises reacting a dihydroxy aromatic compound under interfacial conditions with phosgene and an aliphatic chloroformate. The aliphatic chloroformate is prepared by a method comprising introducing a mixture of at least one aliphatic hydroxyl compound, phosgene, a solvent, and optionally at least one organic base into a flow reactor to obtain a unidirectional flowing reaction mixture. The unidirectional flowing reaction mixture inside the flow reactor is maintained at a temperature between about 0° C. and about 60° C. to produce a product stream comprising an aliphatic chloroformate.

In yet another aspect, the present invention relates to a method for preparing a co-polycarbonate said method comprising reacting at least one dihydroxy aromatic compound under interfacial conditions with phosgene and an oligomeric aliphatic chloroformate. The oligomeric aliphatic chloroformate is prepared by a method comprising introducing into a flow reactor at least one oligomeric aliphatic hydroxyl compound, phosgene, a solvent, and optionally an organic base to form a unidirectional flowing reaction mixture; and maintaining said unidirectional flowing reaction mixture at a temperature inside the flow reactor in a range between about 0° C. and about 60° C. to produce a product stream comprising an oligomeric aliphatic chloroformate.

DETAILED DESCRIPTION OF THE INVENTION

The present invention may be understood more readily by reference to the following detailed description of preferred embodiments of the invention and the examples included therein. In the following specification and the claims which follow, reference will be made to a number of terms which shall be defined to have the following meanings:

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

The modifier "about" used in connection with a quantity is inclusive of the stated value and has the meaning dictated by the context (e.g., includes the degree of error associated with measurement of the particular quantity).

The term "aliphatic hydroxyl compound" as used herein refers to an organic species comprising at least one hydroxyl group attached to a non-aromatic carbon atom. A hydroxyl group attached to a non-aromatic carbon atom is referred to herein as an "aliphatic hydroxyl group". Methanol, ethanol, ethylene glycol, cyclohexanol, sucrose, dextrose, benzyl alcohol, and cholesterol illustrate aliphatic hydroxyl compounds. Conversely, organic species which do not comprise a hydroxyl group attached to a non-aromatic carbon atom are not ranked among aliphatic hydroxyl compounds. Phenol, hydroquinone, beta-naphthol; 1,3,5-trihydroxybenzene; and 3-hydroxypyridine exemplify organic species comprising one or more hydroxyl groups which do not qualify as aliphatic hydroxyl compounds. However, compounds comprising hydroxyl groups attached to both aromatic- and non-aromatic carbon atoms, for example 4-hydroxybenzyl alcohol, fall within the group defined by the term aliphatic hydroxyl compounds.

The term "oligomeric aliphatic hydroxyl compound" as used herein refers to an aliphatic hydroxyl compound having a weight average molecular weight ($M_w$) of less than or equal to 15000 grams per mole as measured by gel permeation chromatography using polystyrene molecular weight standards.

As used herein the term "aliphatic radical" refers to a radical having a valence of at least one comprising a linear or branched array of atoms, which is not cyclic. Examples of aliphatic radicals include methyl, methylene, ethyl, ethylene, hexyl, hexamethylene, and the like.

As used herein the term "cycloaliphatic radical" refers to a radical having a valence of at least one comprising an array of atoms which is cyclic but which is not aromatic. Examples of cycloaliphatic radicals include cyclopropyl, cyclopentyl, cyclohexyl, and the like.

As used herein the term "aromatic radical" refers to a radical having a valence of at least one comprising at least one aromatic group. Examples of aromatic radicals include phenyl, pyridyl, furanyl, thienyl, naphthyl, and the like.

As used herein the term "solvent" refers to a single solvent such as methylene chloride, or in the alternative to mixtures of solvents such as a mixture of methylene chloride and toluene.

"BPA" is herein defined as bisphenol A and is also known as 2,2-bis(4-hydroxyphenyl)propane; 4,4'-isopropylidenediphenol, and p,p-BPA.

As noted, the present invention generally relates to a method of preparing an aliphatic chloroformate. The method includes introducing at least one aliphatic hydroxyl compound, phosgene and a solvent into a flow reactor to form a unidirectional flowing reaction mixture. Optionally, at least one organic base is introduced into the flow reactor. In one embodiment of the present invention, the unidirectional flowing reaction mixture is substantially anhydrous. The term "substantially anhydrous" is defined as containing less than 5% percent by weight of water based on the weight of the reaction mixture comprising aliphatic hydroxyl compound, phosgene and a solvent. When the reaction mixture is not substantially anhydrous, the water may compete with the hydroxyl groups of the aliphatic hydroxyl compound for phosgene. When the hydroxyl groups of the aliphatic hydroxyl compound react with phosgene product chloroformates result, together with by-product hydrochloric acid. However, when water reacts with phosgene the products are carbon dioxide and hydrochloric acid. The presence of water in the unidirectional flowing reaction mixture may be thus undesirable because phosgene is consumed without the production of the desired chloroformate product.

Aliphatic chloroformates which may be prepared according to the present invention include monochloroformates and polychloroformates. Polychloroformates comprise at least two chloroformate groups, for example, bischloroformates, and trischloroformates. In one particular embodiment the aliphatic chloroformate formed is a bischloroformate.

Aliphatic hydroxyl compounds suitable for use according to the present invention include aliphatic hydroxyl compounds having at least one aliphatic hydroxyl group. In one embodiment, the aliphatic hydroxyl compound comprises formula I,

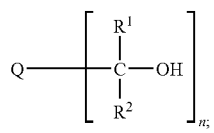

wherein $R^1$ and $R^2$ are independently at each occurrence a hydrogen atom, a $C_1$-$C_5$ aliphatic radical, a $C_3$-$C_7$ cycloaliphatic radical, an $C_3$-$C_6$ aromatic radical, or $R^1$ and $R^2$ may together form a $C_3$-$C_6$ cycloaliphatic radical; Q is a moiety having a total number of positions available for substitution and is a bond, a hydrogen atom, a $C_1$-$C_{10}$ aliphatic radical, a $C_3$-$C_6$ cycloaliphatic radical, or a $C_3$-$C_6$ aromatic radical; and n is a number from 1 to the total number of positions on Q available for substitution. For example, when Q is a bond, and n is 2, and $R^1$ and $R^2$ are hydrogen atoms, the compound defined by structure I is ethylene glycol, wherein because Q is defined as a bond it has zero positions available for substitution. As a further example, when Q is a phenyl ring, n is 1, and $R^1$ and $R^2$ are hydrogen atoms, structure I defines benzyl alcohol, a compound wherein, because Q is defined as a phenyl ring, Q has five positions available for substitution.

Suitable aliphatic hydroxyl compounds include aliphatic mono-alcohols and aliphatic polyols. In certain embodiments the aliphatic hydroxyl compound may also be selected from the group consisting of polymeric aliphatic hydroxy compounds. Polymeric aliphatic hydroxy compounds include oligomeric species, defined herein as having a weight average molecular weight ($M_w$) of less than or equal to 15000 grams per mole as measured by gel permeation chromatography using polystyrene molecular weight standards. Polymeric aliphatic hydroxy compounds also include high molecular weight species oligomeric species, defined herein as having a weight average molecular weight ($M_w$) of greater than 15000 grams per mole as measured by gel permeation chromatography using polystyrene molecular weight standards. Exemplary aliphatic hydroxy compounds include, but are not limited to, 1-hexanol, polyethylene glycol, polytetrahydrofuran diol, polypropylene oxide diol, poly(ethylene-butylene)copolymer diols, trimethylolpropane, isosorbide, cholesterol, menthol, 3-pentanol, tertiary-amyl alcohol, allyl alcohol, propargyl alcohol, ethylene glycol, 1,6-hexanediol and 1,4-butanediol.

The method of the present invention employs phosgene as the chloroformylating agent. Thus, phosgene reacts with the aliphatic hydroxyl groups of the aliphatic hydroxyl compounds employed, to provide aliphatic chloroformates. The molar ratio of phosgene to the aliphatic hydroxyl groups is typically in a range of from about 1.1 to 1 to about 100 to 1. In one embodiment, the molar ratio of phosgene to the aliphatic hydroxyl groups, is in a range of from about 1.1 to 1 to about 50 to 1. In another embodiment, the molar ratio of phosgene to the aliphatic hydroxyl groups is in a range of from about 1.1 to 1 to about 4 to 1.

The chloroformylation reaction is carried out in the presence of a solvent, which helps to maintain the flow of the reaction mixture in the flow reactor and dissipate heat, among other advantages. The solvent is selected from the group consisting of aliphatic solvents and aromatic solvents. In one embodiment the solvent is selected from the group consisting of $C_6$-$C_{10}$ hydrocarbon solvents and $C_1$-$C_{10}$ chlorinated solvents. Exemplary $C_6$-$C_{10}$ hydrocarbon solvents include benzene, toluene, hexane, heptane, octane, isooctane, decane, xylene, mesitylene, and the like. In one embodiment, the solvent is selected from the group consisting of $C_1$-$C_{10}$ chlorinated solvents. Suitable $C_1$-$C_{10}$ chlorinated solvents include methylene chloride, ethylene chloride, chloroform, chorobenzene, chlorotoluene, chloronaphthalene, and the like. Chorinated aliphatic solvents such as methylene chloride are typically preferred.

Optionally, an organic base may be introduced as a component reactant in the unidirectional flowing reaction mixture. The role of the organic base is to mediate the formation of chloroformate groups in the reaction of the aliphatic hydroxy groups with phosgene. The organic base is believed to enhance the rate of reaction between the aliphatic hydroxy groups and phosgene, and to serve as a trap for the HCl by-product in the reaction. The organic base is selected from the group consisting of amine bases and polyamine bases. In one embodiment, the unidirectional flowing reaction mixture is characterized by a molar ratio of the organic base to the aliphatic hydroxyl groups in a range of from about 0.01 to 1 to about 100 to 1. In another embodiment, the unidirectional flowing reaction mixture is characterized by a molar ratio of the organic base to the aliphatic hydroxyl groups in a range of from about 0.01 to 1 to about 50 to 1. In still another embodiment, the unidirectional flowing reaction mixture is characterized by a molar ratio of the organic base to the aliphatic hydroxyl groups in a range of from about 0.01 to 1 to about 5 to 1.

As noted, the method of the present invention comprises introducing into a flow reactor at least one aliphatic hydroxyl compound, phosgene, a solvent, and optionally an organic base to form a unidirectional flowing reaction mixture in which a product aliphatic chloroformate is formed. For convenience, the aliphatic hydroxyl compound, phosgene, and the organic base are collectively referred to as "the reactants". The reactants and solvent are typically introduced continuously into the flow reactor to produce a flowing reaction mixture. Continuous introduction of the reactants and solvent is not required, however. In one embodiment, the introduction of one or more of the aliphatic hydroxyl compounds, phosgene, a solvent, and optionally an organic base is carried out in a non-continuous manner. For example, the phosgene may be introduced in a series of discrete pulses with a time interval between each individual introduction of phosgene. The time intervals may be regular time intervals (i.e. be time intervals of equal duration), irregular time intervals, or a combination thereof.

The rates of addition of one or more of the reactants and solvent may be controlled by feedback provided by one or more sensors located within the flow reactor or in the product stream after it emerges from the flow reactor. For example, an excursion in the reactor effluent chloroformate concentration may trigger a change in the rate of addition of one or more of the reactants, for example the organic base.

The flow reactor used for carrying out the chloroformylation reaction is typically a tube having a front end into which the reactants and solvent are introduced, and a back end from which a product stream emerges from the reactor, but is not limited to tube reactors or tubular reactors. Many types of flow reactors are known and can be used in the practice of the present invention. For example the flow reactor may be a multi-channel flow reactor having a plurality of channels through which the flowing reaction mixture passes. In one embodiment, the flow reactor is continuous stirred tank reactor (CSTR). In another embodiment, the flow reactor is a tubular reactor configured with a continuous stirred tank reactor such that the output from the tubular reactor serves as the input for the CSTR. In one embodiment, the flow reactor comprises a single channel having a rectangular-shaped cross section.

Within the flow reactor, a unidirectional flowing reaction mixture is produced. Although mixing elements may be present within the flow reactor, the flowing reaction mixture flows essentially in one direction, i.e. from the front end of the reactor to the back end of the reactor. This condition is sometimes also referred to as "co-current flow". A unidirectional flowing reaction mixture characterized by co-current flow is typically formed by introducing reactants and solvent into an upstream portion of a flow reactor and removing at a position downstream a product stream containing all of the unreacted reactants, solvent, products, and by-products. The flow reactor may be equipped with a single inlet at the front end of the reactor for the introduction of reactants and solvent. Alternatively, the reactor may comprise a plurality of inlets for the introduction of reactants and solvents. As the unidirectional flowing reaction mixture passes through the flow reactor, the reactants are converted to products and by-products. Typically, the product is the aliphatic chloroformate and the by-product hydrochloric acid. When an organic base is present the by-product hydrochloric acid is converted to the hydrochloride salt of the organic base. The unidirectional flowing reaction mixture in which a substantial portion of the reactants have been converted to product and by-product is referred to as the product stream. The flow reactor has at least one reactor outlet through which the product stream emerges from the reactor. Alternatively, the flow reactor may comprise a plurality of reactor outlets. The product stream exits from the reactor outlet or outlets. Typically, no vent or waste streams different from the product stream exit any separate reactor outlet—only the product stream exits, albeit possibly at multiple reactor outlets. The term, "single product stream" means that the entire product stream comprising all of the unreacted reactants (i.e. unreacted starting materials), products, by-products and solvent emerges from the reactor through a single reactor outlet. As a consequence, the entire mass of the reactants and solvent is conserved within the single product stream emerging from the flow reactor.

Alternatively, the flow reactor used may comprise a plurality of reactor outlets through which the product stream emerges. For example, in one embodiment the flow reactor is a tubular reactor of length "L" measured from the front end of the reactor to the back end of the reactor, said tubular reactor having two reactor outlets, a first reactor outlet located a distance "L/2" from the front end of the reactor, and a second reactor outlet located a distance "L" from the front end of the reactor. Reactants and solvent are introduced through three separate inlets at the front end of the reactor. The rates of addition of reactants and solvent and the reactor temperature may be controlled such that the product stream emerging at the first reactor outlet is characterized by a percent conversion of reactants to products of about 50 percent, and that the product stream emerging from the second reactor outlet is characterized by a percent conversion of reactants to products of about 100 percent. Each of the two product streams exiting the tubular flow reactor at positions "L/2" and "L" respectively contains all of the unreacted reactants, (i.e. unreacted starting materials), products, by-products and solvent present in the product stream at positions "L/2" and "L" within the flow reactor. It should be noted as well that the sum of the masses of the two product streams emerging at positions "L/2" and "L" is equal to the mass of reactants and solvents introduced into the tubular reactor. Thus, the entire mass of the reactants and solvent is conserved within the two streams emerging at various points along the flow reactor.

It should be further noted that the temperature in various sections of the reactor may be the same or different. For example, in the tubular reactor system just described the temperature of the flowing reaction mixture at first reactor outlet located a distance "L/2" from the front end of the reactor may be 25° C. while at the second reactor outlet located a distance "L" from the front end of the reactor the temperature of the flowing reaction mixture is 54° C. In addition, the flow reactor may be uniformly heated or uniformly cooled. Alternatively, the reaction may be carried out under adiabatic conditions.

Where multiple product streams are produced by a flow reactor according to the present invention it will be appreciated by those skilled in the art that each of the product streams may be used for a different purpose; as for example in the tubular reactor system just described the product stream emerging at the first reactor outlet located a distance "L/2" from the front end of the reactor may be directed to a polymerization reactor and used in the preparation of a co-polycarbonate, while at the product stream emerging at the second reactor outlet located a distance "L" from the front end of the reactor may be used to provide a purified chloroformate.

As noted, the flow reactor is not particularly limited and may be any reactor system, which provides for the "upstream" introduction of the reactants and the "downstream" removal of the product stream comprising the aliphatic chloroformate, the solvent, the by-product HCl (or the hydrochloride salt of the organic base), and any unreacted reactants. The flow reactor may comprise a series of flow reactor components, as for example, a series of continuous flow reactors arrayed such that the effluent from a first flow reactor provides the input for a second flow reactor and so forth. The reactants may be introduced into the flow reactor system through one or more feed inlets attached to the flow reactor system. Typically, it is preferred that the reactants and solvent be introduced into the flow reactor through at least three feed inlets. For example, as in the case where a solution of the aliphatic hydroxyl compound in an organic solvent such as methylene chloride, optional organic base, and phosgene are introduced through separate feed inlets at or near the upstream end of a flow reactor. Alternatively, the feed solution may comprise a mixture of aliphatic hydroxyl compound, solvent and the optional base, while phosgene is fed in separately. Alternative arrangements wherein one or more of the reactants is introduced through multiple feed inlets at various points along the flow reactor are also possible. Typically, the relative amounts of the reactants and solvent present in the flow reactor are controlled by the rate at which they are introduced. For example, a reactant can be introduced into the flow reactor through pumps calibrated to deliver a particular number of moles of said reactant per unit time.

In one embodiment the present invention provides a method for preparing a co-polycarbonate. The method comprises reacting a dihydroxy aromatic compound under interfacial conditions with phosgene and an aliphatic chloroformate. The term "interfacial conditions" is meant to describe the conditions typically used to prepare polycarbonates commercially, namely conditions under which a mixture comprising the salt of a dihydroxy aromatic compound, base, water and a water immiscible solvent are reacted in a two phase reaction mixture with phosgene to afford polycarbonate. Thus in one embodiment, an aliphatic chloroformate prepared by the method of the present invention is reacted under interfacial conditions with a dihydroxy aromatic compound and phosgene to afford a co-polycarbonate. Typically, the interfacial polymerization is carried out at a temperature between about 25° C. and about 40° C. at atmospheric pressure under relatively high pH conditions of 8-14, preferably pH 10-14. Generally an acid scavenger is employed which neutralizes the hydrogen chloride formed during the interfacial reaction. Typically the acid scavenger used is an aqueous base, for example, an alkali metal hydroxide. Non-limiting examples of alkali metal hydroxides include sodium hydroxide and potassium hydroxide. In a preferred embodiment the alkali metal hydroxide is sodium hydroxide. A catalyst is employed to promote the interfacial reaction and high yields are generally obtained. Typically, catalysts that may be employed herein are preferably amine catalysts. In one particular embodiment the catalyst is triethylamine (TEA). As noted, the aliphatic chloroformate is prepared by the method of the present invention wherein at least one aliphatic hydroxyl compound, phosgene, a solvent, and optionally an organic base are introduced into a flow reactor to form a unidirectional flowing reaction mixture. The unidirectional flowing reaction mixture is particular embodiments substantially anhydrous and is maintained at a temperature in a range between about 0° C. and about 60° C. to produce a product stream comprising an aliphatic chloroformate and by-product HCl or the hydrochloride salt of the optional organic base. In a preferred embodiment unidirectional flowing reaction mixture is substantially anhydrous and the temperature is maintained in a range between about 10° C. and about 50° C.

In another embodiment the present invention relates to a method for preparing a co-polycarbonate said method comprising reacting at least one dihydroxy aromatic compound under interfacial conditions with phosgene and an oligomeric aliphatic chloroformate, typically an organic, prepared by the method of the present invention, for example the bischloroformate of polyethylene glycol having a weight average molecular weight of about 5000 grams per mole.

In one embodiment the oligomeric aliphatic hydroxyl compound is selected from the group consisting of oligomeric ethylene-butylene copolymer diols, polyethylene glycol, polyethylene glycol monoethers, polytetrahydrofuran diol, polypropylene oxide diol, and mixtures thereof.

In one embodiment the dihydroxy aromatic compound is a bisphenol having formula II,

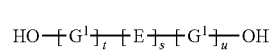

Formula II wherein each $G^1$ is independently at each occurrence a $C_6$-$C_{20}$ aromatic radical; E is independently at each occurrence a bond, a $C_3$-$C_{20}$ cycloaliphatic radical, a $C_3$-$C_{20}$ aromatic radical, a $C_1$-$C_{20}$ aliphatic radical, a sulfur-containing linkage, a selenium-containing linkage, a phosphorus-containing linkage, or an oxygen atom; "t" is a number greater than or equal to one; "s" is either zero or one; and "u" is a whole number including zero.

In certain embodiments the bisphenol is selected from the group consisting of 1,1-bis(4-hydroxyphenyl)cyclopentane; 2,2-bis(3-allyl-4-hydroxyphenyl)propane; 2,2-bis(2-t-butyl-4-hydroxy-5-methylphenyl)propane; 2,2-bis(3-t-butyl-4-hydroxy-6-methylphenyl)propane; 2,2-bis(3-t-butyl-4-hydroxy-6-methylphenyl)butane; 1,3-bis[4-hydroxyphenyl-1-(1-methylethylidine)]benzene; 1,4-bis[4-hydroxyphenyl-1-(1-methylethylidine)]benzene; 1,3-bis[3-t-butyl-4-hydroxy-6-methylphenyl-1-(1-methylethylidine)]benzene; 1,4-bis[3-t-butyl-4-hydroxy-6-methylphenyl-1-(1-methylethylidine)]benzene; 4,4'-biphenol; 2,2',6,8-tetramethyl-3,3',5,5'-tetrabromo-4,4'-biphenol; 2,2',6,6'-tetramethyl-3,3',5-tribromo-4,4'-biphenol; 1,1-bis(4-hydroxyphenyl)-2,2,2-trichloroethane; 1,1-bis(4-hydroxyphenyl)-1-cyanoethane; 1,1-bis(4-hydroxyphenyl)dicyanomethane; 1,1-bis(4-hydroxyphenyl)-1-cyano-1-phenylmethane; 2,2-bis(3-methyl-4-hydroxyphenyl)propane; 1,1-bis(4-hydroxyphenyl)norbornane; 3,3-bis(4-hydroxyphenyl)phthalide; 1,2-bis(4-hydroxyphenyl)ethane; 1,3-bis(4-hydroxyphenyl)propenone; bis(4-hydroxyphenyl)sulfide; 4,4'-oxydiphenol; 4,4-bis(4-hydroxyphenyl)pentanoic acid; 4,4-bis(3,5-dimethyl-4-hydroxyphenyl)pentanoic acid; 2,2-bis(4-hydroxyphenyl) acetic acid; 2,4'-dihydroxydiphenylmethane; 2-bis(2-hydroxyphenyl)methane; bis(4-hydroxyphenyl)methane; bis(4-hydroxy-5-nitrophenyl)methane; bis(4-hydroxy-2,6-dimethyl-3-methoxyphenyl)methane; 1,1-bis(4-hydroxyphenyl)ethane; 1,1-bis(4-hydroxy-2-chlorophenyl)ethane; 2,2-bis(4-hydroxyphenyl)propane (bisphenol-A); 1,1-bis(4-hydroxyphenyl)propane; 2,2-bis(3-chloro-4-hydroxyphenyl)propane; 2,2-bis(3-bromo-4-hydroxyphenyl)propane; 2,2-bis(4-hydroxy-3-methylphenyl)propane; 2,2-bis(4-hydroxy-3-isopropylphenyl)propane; 2,2-bis(3-t-butyl-4-hydroxyphenyl)propane; 2,2-bis(3-phenyl-4-hydroxyphenyl)propane; 2,2-bis(3,5-dichloro-4-hydroxyphenyl)propane; 2,2-bis(3,5-dibromo-4-hydroxyphenyl)propane; 2,2-bis(3,5-dimethyl-4-hydroxyphenyl)propane; 2,2-bis(3-chloro-4-hydroxy-5-methylphenyl)propane; 2,2-bis(3-bromo-4-hydroxy-5-methylphenyl)propane; 2,2-bis(3-chloro-4-hydroxy-5-isopropylphenyl)propane; 2,2-bis(3-bromo-4-hydroxy-5-isopropylphenyl)propane; 2,2-bis(3-t-butyl-5-chloro-4-hydroxyphenyl)propane; 2,2-bis(3-bromo-5-t-butyl-4-hydroxyphenyl)propane; 2,2-bis(3-chloro-5-phenyl-4-hydroxyphenyl)propane; 2,2-bis(3-bromo-5-phenyl-4-hydroxyphenyl)propane; 2,2-bis(3,5-disopropyl-4-hydroxyphenyl)propane; 2,2-bis(3,5-di-t-butyl-4-hydroxyphenyl)propane; 2,2-bis(3,5-diphenyl-4-hydroxyphenyl)propane; 2,2-bis(4-hydroxy-2,3,5,6-tetrachlorophenyl)propane; 2,2-bis(4-hydroxy-2,3,5,6-tetrabromophenyl)propane; 2,2-bis(4-hydroxy-2,3,5,6-tetramethylphenyl)propane; 2,2-bis(2,6-dichloro-3,5-dimethyl-4-hydroxyphenyl)propane; 2,2-bis(2,6-dibromo-3,5-dimethyl-4-hydroxyphenyl)propane; 2,2-bis(4-hydroxy-3-ethylphenyl)propane; 2,2-bis(4-hydroxy-3,5- dimethylphenyl)propane; 2,2-bis(3,5,3',5'-tetrachloro-4,4'-dihydroxyphenyl)propane; 1,1-bis(4-hydroxyphenyl)cyclohexylmethane; 2,2-bis(4-hydroxyphenyl)-1-phenylpropane; 1,1-bis(4-hydroxyphenyl)cyclohexane; 1,1-bis(3-chloro-4-hydroxyphenyl)cyclohexane; 1,1-bis(3-bromo-4-hydroxyphenyl)cyclohexane; 1,1-bis(4-hydroxy-3-methylphenyl)cyclohexane; 1,1-bis(4-hydroxy-3-isopropylphenyl)cyclohexane; 1,1-bis(3-t-butyl-4-hydroxyphenyl)cyclohexane; 1,1-bis(3-phenyl-4-hydroxyphenyl)cyclohexane; 1,1-bis(3,5-dichloro-4-hydroxyphenyl)cyclohexane; 1,1-bis(3,5-dibromo-4-hydroxyphenyl)cyclohexane; 1,1-bis(3,5-dimethyl-4-hydroxyphenyl)cyclohexane; 4,4'-[1-methyl-4-(1-methyl-ethyl)-1,3-cyclohexandiyl]bisphenol (1,3 BHPM); 4-[1-[3-(4-hydroxyphenyl)-4-methylcyclohexyl]-1-methyl-ethyl]-phenol (2,8 BHPM); 3,8-dihydroxy-5a,10b-diphenylcoumarano-2',3',2,3-coumarane (DCBP); 2-phenyl-3,3-bis(4-hydroxyphenyl)phthalimidine; 1,1-bis(3-chloro-4-hydroxy-5-methylphenyl)cyclohexane; 1,1-bis(3-bromo-4-hydroxy-5-methylphenyl)cyclohexane; 1,1-bis(3-chloro-4-hydroxy-5-isopropylphenyl)cyclohexane; 1,1-bis(3-bromo-4-hydroxy-5-isopropylphenyl)cyclohexane; 1,1-bis(3-t-butyl-5-chloro-4-hydroxyphenyl)cyclohexane; 1,1-bis(3-bromo-5-t-butyl-4-hydroxyphenyl)cyclohexane; 1,1-bis(3-chloro-5-phenyl-4-hydroxyphenyl)cyclohexane; 1,1-bis(3-bromo-5-phenyl-4-hydroxyphenyl)cyclohexane; 1,1-bis(3,5-disopropyl-4-hydroxyphenyl)cyclohexane; 1,1-bis(3,5-di-t-butyl-4-hydroxyphenyl)cyclohexane; 1,1-bis(3,5-diphenyl-4-hydroxyphenyl)cyclohexane; 1,1-bis(4-hydroxy-2,3,5,6-tetrachlorophenyl)cyclohexane; 1,1-bis(4-hydroxy-2,3,5,6-tetrabromophenyl)cyclohexane; 1,1-bis(4-hydroxy-2,3,5,6-tetramethylphenyl)cyclohexane; 1,1-bis(2,6-dichloro-3,5-dimethyl-4-hydroxyphenyl)cyclohexane; 1,1-bis(2,6-dibromo-3,5-dimethyl-4-hydroxyphenyl)cyclohexane; 1,1-bis(4-hydroxyphenyl)-3,3,5-trimethylcyclohexane; 1,1-bis(3-chloro-4-hydroxyphenyl)-3,3,5-trimethylcyclohexane; 1,1-bis(3-bromo-4-hydroxyphenyl)-3,3,5-trimethylcyclohexane; 1,1-bis(4-hydroxy-3-methylphenyl)-3,3,5-trimethylcyclohexane; 1,1-bis(4-hydroxy-3-isopropylphenyl)-3,3,5-trimethylcyclohexane; 1,1-bis(3-t-butyl-4-hydroxyphenyl)-3,3,5-trimethylcyclohexane; 1,1-bis(3-phenyl-4-hydroxyphenyl)-3,3,5-trimethylcyclohexane; 1,1-bis(3,5-dichloro-4-hydroxyphenyl)-3,3,5-trimethylcyclohexane; 1,1-bis(3,5-dibromo-4-hydroxyphenyl)-3,3,5-trimethylcyclohexane; 1,1-bis(3,5-dimethyl-4-hydroxyphenyl)-3,3,5-trimethylcyclohexane; 1,1-bis(3-chloro-4-hydroxy-5-methylphenyl)-3,3,5-trimethylcyclohexane; 1,1-bis(3-bromo-4-hydroxy-5-methylphenyl)-3,3,5-trimethylcyclohexane; 1,1-bis(3-chloro-4-hydroxy-5-isopropylphenyl)-3,3,5-trimethylcyclohexane; 1,1-bis(3-bromo-4-hydroxy-5-isopropylphenyl)-3,3,5-trimethylcyclohexane; 1,1-bis(3-t-butyl-5-chloro-4-hydroxyphenyl)-3,3,5-trimethylcyclohexane; 1,1-bis(3-bromo-5-t-butyl-4-hydroxyphenyl)-3,3,5-trimethylcyclohexane; bis(3-chloro-5-phenyl-4-hydroxyphenyl)-3,3,5-trimethylcyclohexane; 1,1-bis(3-bromo-5-phenyl-4-hydroxyphenyl)-3,3,5-trimethylcyclohexane; 1,1-bis(3,5-disopropyl-4-hydroxyphenyl)-3,3,5-trimethylcyclohexane; 1,1-bis(3,5-di-t-butyl-4-hydroxyphenyl)-3,3,5-trimethylcyclohexane; 1,1-bis(3,5-diphenyl-4-hydroxyphenyl)-3,3,5-trimethylcyclohexane; 1,1-bis(4-hydroxy-2,3,5,6-tetrachlorophenyl)-3,3,5-trimethylcyclohexane; 1,1-bis(4-hydroxy-2,3,5,6-tetrabromophenyl)-3,3,5-trimethylcyclohexane; 1,1-bis(4-hydroxy-2,3,5,6-tetramethylphenyl)-3,3,5-trimethylcyclohexane; 1,1-bis(2,6-dichloro-3,5-dimethyl-4-hydroxyphenyl)-3,3,5-trimethylcyclohexane; 1,1-bis(2,6-dibromo-3,5-dimethyl-4-hydroxyphenyl)-3,3,5-trimethylcyclohexane; 4,4-bis(4-hydroxyphenyl)heptane; 1,1-bis(4-hydroxyphenyl)decane; 1,1-bis(4-hydroxyphenyl)cyclododecane; 1,1-bis(3,5-dimethyl-4-hydroxyphenyl)cyclododecane; 4,4'dihydroxy-1,1-biphenyl; 4,4'-dihydroxy-3,3'-dimethyl-1,1-biphenyl; 4,4'-dihydroxy-3,3'-dioctyl-1,1-biphenyl; 4,4'-(3,3,5-trimethylcyclohexylidene)diphenol; 4,4'-bis(3,5-dimethyl)diphenol; 4,4'-dihydroxydiphenylether; 4,4'-dihydroxydiphenylthioether; 1,3-bis(2-(4-hydroxyphenyl)-2-propyl)benzene; 1,3-bis(2-(4-hydroxy-3-methylphenyl)-2-propyl)benzene; 1,4-bis(2-(4-hydroxyphenyl)-2-propyl)benzene; 1,4-bis(2-(4-hydroxy-3-methylphenyl)-2-propyl)benzene; 2,4'-dihydroxyphenyl sulfone; 4,4'-dihydroxydiphenylsulfone (BPS); bis(4-hydroxyphenyl)methane; 2,6-dihydroxy naphthalene; hydroquinone; resorcinol; $C_{1-3}$ alkyl-substituted resorcinols; 3-(4-hydroxyphenyl)-1,1,3-trimethylindan-5-ol; 1-(4-hydroxyphenyl)-1,3,3-trimethylindan-5-ol; 4,4-dihydroxydiphenyl ether; 4,4-dihydroxy-3,3-dichlorodiphenylether; 4,4-dihydroxy-2,5-dihydroxydiphenyl ether; 4,4-thiodiphenol; 2,2,2',2'-tetrahydro-3,3,3',3'-tetramethyl-1,1'-spirobi[1H-indene]-6,6'-diol; and mixtures thereof.

In one embodiment of the present invention, the co-polycarbonates prepared using the aliphatic chloroformates of the present invention may be further employed to prepare polymer compositions. In one embodiment, the polymer compositions provided by the present invention comprise one or more additional resins selected from the group consisting of polyamides, polyesters, polycarbonates; olefin polymers such as ABS, polystyrene, polyethylene; polysiloxanes, polysilanes and polysulfones. In certain embodiments the one or more additional resins may be present preferably in an amount less than or equal to 40 weight percent, more preferably less than or equal to 35 weight percent and most preferably less than or equal to about 30 weight percent based on the total weight of the polymer composition.

The polymer compositions may contain various additives, which may be used alone or in combination. These additives include such materials as thermal stabilizers, antioxidants, UV stabilizers, plasticizers, visual effect enhancers, extenders, antistatic agents, catalyst quenchers, mold releasing agents, fire retardants, blowing agents, impact modifiers and processing aids. The different additives that can be incorporated in the polymer compositions of the present invention are typically commonly used and known to those skilled in the art.

Visual effect enhancers, sometimes known as visual effects additives or pigments may be present in an encapsulated form, a non-encapsulated form, or laminated to a particle comprising polymeric resin. Some non-limiting examples of visual effects additives are aluminum, gold, silver, copper, nickel, titanium, stainless steel, nickel sulfide, cobalt sulfide, manganese sulfide, metal oxides, white mica, black mica, pearl mica, synthetic mica, mica coated with titanium dioxide, metal-coated glass flakes, and colorants, including but not limited to, Perylene Red. The visual effect additive may have a high or low aspect ratio and may comprise greater than 1 facet. Dyes may be employed such as Solvent Blue 35, Solvent Blue 36, Disperse Violet 26, Solvent Green 3, Anaplast Orange LFP, Perylene Red, and Morplas Red 36. Fluorescent dyes may also be employed including, but not limited to, Permanent Pink R (Color Index Pigment Red 181, from Clariant Corporation), Hostasol Red 5B (Color Index #73300, CAS # 522-75-8, from Clariant Corporation) and Macrolex Fluorescent Yellow 10GN (Color Index Solvent Yellow 160:1, from Bayer Corporation). Pigments such as titanium dioxide, zinc sulfide, carbon black, cobalt chromate, cobalt titanate, cadmium sulfides, iron oxide, sodium aluminum sulfosilicate, sodium sulfosilicate, chrome antimony titanium rutile, nickel antimony titanium rutile, and zinc oxide may be employed. Visual effect additives in encapsulated form usually comprise a visual effect material such as a high aspect ratio material like aluminum flakes encapsulated by a polymer. The encapsulated visual effect additive has the shape of a bead.

Non-limiting examples of antioxidants that can be used in the polymer compositions of the present invention include tris(2,4-di-tert-butylphenyl)phosphite; 3,9-di(2,4-di-tert-butylphenoxy)-2,4,8,10-tetraoxa-3,9-diphosphaspiro[5.5]undecane; 3,9-di(2,4-dicumylphenoxy)-2,4,8,10-tetraoxa-3,9-diphosphaspiro[5.5]undecane; tris(p-nonylphenyl) phosphite; 2,2',2''-nitrilo[triethyl-tris[3,3',5,5'-tetra-tertbutyl-1,1'-biphenyl-2'-diyl]phosphite]; 3,9-distearyloxy-2,4,8,10-tetraoxa-3,9-diphosphaspiro[5.5]undecane; dilauryl phosphite; 3,9-di[2,6-di-tert-butyl-4-methylphenoxy]-2,4,8,10-tetraoxa-3,9-diphosphaspiro[5.5]undecane; tetrakis(2,4-di-tert-butylphenyl) -4,4'-bis(diphenylene)phosphonite; distearyl pentaerythritol diphosphite; diisodecyl pentaerythritol diphosphite; 2,4,6-tri-tert-butylphenyl-2-butyl -2-ethyl-1,3-propanediol phosphite; tristearyl sorbitol triphosphite; tetrakis(2,4-di-tert-butylphenyl) -4,4'-biphenylene diphosphonite; (2,4,6-tri-tert-butylphenyl)-2-butyl -2-ethyl-1,3-propanediolphosphite; triisodecylphosphite; and mixtures of phosphites containing at least one of the foregoing.

The thermoplastic composition may optionally comprise an impact modifier. The impact modifier resin added to the thermoplastic composition in an amount corresponding to about 1% to about 30% by weight, based on the total weight of the composition. Suitable impact modifiers include those comprising one of several different rubbery modifiers such as graft or core shell rubbers or combinations of two or more of these modifiers. Impact modifiers are illustrated by acrylic rubber, ASA rubber, diene rubber, organosiloxane rubber, ethylene propylene diene monomer (EPDM) rubber, styrene-butadiene-styrene (SBS) rubber, styrene-ethylene-butadiene-styrene (SEBS) rubber, acrylonitrile-butadiene-styrene (ABS) rubber, methacrylate-butadiene-styrene (MBS) rubber, styrene acrylonitrile copolymer and glycidyl ester impact modifier.

The term "acrylic rubber modifier" may refer to multi-stage, core-shell, interpolymer modifiers having a cross-linked or partially crosslinked (meth)acrylate rubbery core phase, preferably butyl acrylate. Associated with this cross-linked acrylic ester core is an outer shell of an acrylic or styrenic resin, preferably methyl methacrylate or styrene, which interpenetrates the rubbery core phase. Incorporation of small amounts of other monomers such as acrylonitrile or (meth)acrylonitrile within the resin shell also provides suitable impact modifiers. The interpenetrating network is provided when the monomers forming the resin phase are polymerized and cross-linked in the presence of the previously polymerized and cross-linked (meth)acrylate rubbery phase.

Suitable impact modifiers are graft or core shell structures with a rubbery component with a Tg below 0° C., preferably between about −40° to −80° C., composed of poly alkylacrylates or polyolefins grafted with polymethylmethacrylate (PMMA) or styrene acrylonitrile (SAN). Preferably the rubber content is at least 10 wt %, more preferably greater than 40 wt %, and most preferably between about 40 and 75 wt %.

Other suitable impact modifiers are the butadiene core-shell polymers of the type available from Rohm & Haas, for example Paraloid® EXL2600. Most suitable impact modifier will comprise a two stage polymer having a butadiene based rubbery core and a second stage polymerized from methylmethacrylate alone or in combination with styrene. Other suitable rubbers are the ABS types Blendex® 336 and 415, available from GE Specialty Chemicals. Both rubbers are based on impact modifier resin of SBR rubber. Although several rubbers have been described, many more are commercially available. Any rubber may be used as an impact modifier as long as the impact modifier does not negatively impact the physical or aesthetic properties of the thermoplastic composition.

Non-limiting examples of processing aids that can be used include Doverlube® FL-599 (available from Dover Chemical Corporation), Polyoxyter® (available from Polychem Alloy Inc.), Glycolube P (available from Lonza Chemical Company), pentaerythritol tetrastearate, Metablen A-3000 (available from Mitsubishi Rayon), neopentyl glycol dibenzoate, and the like.

Non-limiting examples of UV stabilizers that can be used include 2-(2'-Hydroxyphenyl)-benzotriazoles, e.g., the 5'-methyl-; 3',5'-di-tert.-butyl-; 5'-tert.-butyl-; 5'-(1,1,3,3-tetramethylbutyl)-; 5-chloro-3',5'-di-tert.-butyl-; 5-chloro-3'-tert.-butyl -5'-methyl-; 3'-sec.-butyl-5'-tert.-butyl-; 3'-alpha-methylbenzyl-5'-methyl; 3'-alpha-methylbenzyl -5'-methyl-5-chloro-; 4'-hydroxy-; 4'-methoxy-; 4'-octoxy-; 3',5'-di-tert.-amyl-; 3'-methyl-5'-carbomethoxyethyl-; 5-chloro-3',5'-di-tert.-amyl-derivatives; and Tinuvin® 234 (available from Ciba Specialty Chemicals). Also suitable are the 2,4-bis-(2'-hydroxyphenyl)-6-alkyl-s-triazines, e.g., the 6-ethyl-; 6-heptadecyl- or 6-undecyl-derivatives. 2-Hydroxybenzophenones e.g., the 4-hydroxy-; 4-methoxy-; 4-octoxy-; 4-decyloxy-; 4-dodecyloxy-; 4-benzyloxy-; 4,2',4'-trihydroxy-; 2,2',4,4'-tetrahydroxy- or 2'-hydroxy-4,4'-dimethoxy-derivative. 1,3-bis-(2'-Hydroxybenzoyl)-benzenes, e.g., 1,3-bis-(2'-hydroxy-4'-hexyloxy-benzoyl)-benzene; 1,3-bis-(2'-hydroxy -4'-octyloxy-benzoyl)-benzene or 1,3-bis-(2'-hydroxy-4'-dodecyloxybenzoyl)-benzene may also be employed. Esters of optionally substituted benzoic acids, e.g., phenylsalicylate; octylphenylsalicylate; dibenzoylresorcin; bis-(4-tert.-butylbenzoyl)-resorcin; benzoylresorcin; 3,5-di-tert.-butyl-4-hydroxybenzoic acid-2,4-di-tert.-butylphenyl ester or -octadecyl ester or -2-methyl-4,6-di-tert.-butyl ester may likewise be employed. Acrylates, e.g., alpha-cyano-beta, beta-diphenylacrylic acid-ethyl ester or isooctyl ester, alpha-carbomethoxy-cinnamic acid methyl ester, alpha-cyano-beta-methyl-p-methoxy-cinnamic acid methyl ester or -butyl ester or N(beta-carbomethoxyvinyl) -2-methyl-indoline may likewise be employed. Oxalic acid diamides, e.g., 4,4'-di-octyloxy-oxanilide; 2,2'-di-octyloxy-5,5'-di-tert.-butyl-oxanilide; 2,2'-di-dodecyloxy-5,5-di-tert.-butyl-oxanilide; 2-ethoxy-2'-ethyl-oxanilide; N,N'-bis-(3-dimethyl-aminopropyl)-oxalamide; 2-ethoxy-5-tert.-butyl-2'-ethyloxanilide and the mixture thereof with 2-ethoxy-2'-ethyl-5,4'-di-tert.-butyl-oxanilide; or mixtures of ortho- and para-methoxy- as well as of o- and p-ethoxy-disubstituted oxanilides are also suitable as UV stabilizers. Preferably the ultraviolet light absorber used in the instant compositions is 2-(2-hydroxy-5-methylphenyl)-2H-benzotriazole; 2-(2-hydroxy-3,5-di-tert-amylphenyl)-2H-benzotriazole; 2-[2-hydroxy -3,5-di-(alpha, alpha-dimethylbenzyl)phenyl]-2H-benzotriazole; 2-(2-hydroxy-5-tert-octylphenyl) -2H-benzotriazole; 2-hydroxy-4-octyloxybenzophenone; nickel bis(O-ethyl 3,5-di-tert-butyl-4-hydroxybenzylphosphonate); 2,4-dihydroxybenzophenone; 2-(2-hydroxy-3-tert-butyl-5-methylphenyl)-2H-benzotriazole; nickel butylamine complex with 2,2'-thiobis(4-tert-butylphenol); 2-ethoxy-2'-ethyloxanilide; 2-ethoxy -2'-ethyl-5,5'-ditert-butyloxanilide or a mixture thereof.

Non-limiting examples of fire retardants that can be used include potassium diphenylsulfone sulfonate, and phosphite esters of polyhydric phenols, such as resorcinol and bisphenol A.

Non-limiting examples of mold release compositions include esters of long-chain aliphatic acids and alcohols such as pentaerythritol, guerbet alcohols, long-chain ketones, siloxanes, alpha.-olefin polymers, long-chain alkanes and hydrocarbons having 15 to 600 carbon atoms.

EXAMPLES

The following examples are set forth to provide those of ordinary skill in the art with a detailed description of how the methods claimed herein are evaluated, and are not intended to limit the scope of what the inventors regard as their invention. Unless indicated otherwise, parts are by weight, temperature is in ° C.

Molecular weights are reported as number average ($M_n$) or weight average ($M_w$) molecular weight and were determined by gel permeation chromatography (GPC) analysis, using polystyrene molecular weight standards to construct a standard calibration curve against which polymer molecular weights were determined. The temperature of the gel permeation columns was about 25° C. and the mobile phase was chloroform.

In interfacial polymerization reactions a Mettler glass electrode was used to maintain the pH at the appropriate value. The electrode was calibrated at pH 7 and pH 10 using standard pH buffer solutions.

Examples 1-20

The general procedure for the preparation of aliphatic chloroformates in Examples 1-20 is detailed below. A feed solution of alcohol (ROH) in methylene chloride was prepared. In some reactions the system was free of triethylamine (TEA) organic base while in some reactions an appropriate level of triethylamine organic base was added to this solution. When the triethylamine organic base was used, the organic base was co-fed into the flow reactor using a separate feed solution. Phosgene was introduced into the reactor at a specific flow rate, independent of other reactants. The flow reactor employed typically comprised a series of five Ko-Flo® static mixers (7 inches by ¼ inches each). The total reactor volume was about 15 mL. Residence time in the flow reactor varied depending on the flow rates of the components being fed and number of mixing sections used. The product mixture was discharged at the end of the reactor and was conveyed via a three-way valve to a reaction vessel adapted for interfacial polymerization reaction with bisphenol-A, the product chloroformate and phosgene. Alternatively, the product mixture was subjected to analysis to determine the yield of product chloroformate. The system comprising the flow reactor and the reaction vessel adapted for interfacial polymerization was vented to the atmosphere through a caustic scrubber at atmospheric pressure to destroy unreacted phosgene. Results are given in Table 1 below. The amount of chloroformate formed in the flow reactor was determined using several different methods and the method used in a particular experiment is indicated in Table 1 by the superscripts "a", "b", and "c".

Method (a): The product mixture emerging from the flow reactor was reacted with excess diisobutylamine and the product containing an N,N-diisobutyl carbamate derived from the chloroformate was analyzed by $^1$H-NMR. Integration of the signals assigned on the basis of analytical standards to the alpha protons of unreacted alcohol starting material, product carbamate, and symmetrical aliphatic carbonate provided the amounts of each of these components present.

Method (b): The product mixture emerging from the flow reactor was collected over 1N HCl to quench the reaction. The quenched reaction mixture was then analyzed by $^1$H-NMR.

Method (c): The product mixture emerging from the flow reactor was reacted with an excess of sodium phenoxide or sodium p-cumyl phenoxide to convert the product aliphatic chloroformate to a mixed carbonate. The reaction was carried out in methylene chloride. Upon completion of the reaction the methylene chloride was removed under reduced pressure and the residue was analyzed in $CDCl_3$ by $^1$H-NMR.

Each of the analytic methods (a), (b) and (c) afforded was shown to be reliable in model systems using mixtures containing known amounts of alcohols, chloroformates and carbonates.

TABLE I

| Examples | Alcohol | MW, g/mol | moles phosgene/ Alcohol | moles TEA/ Alcohol | Alcohol soln wt % | Soln feed rate (g/min) | Tube Sections | Phosgene Feed rate (gm/min) | Residence Time (sec) | % alcohol conversion to chloroformate | % conversion to carbonate |
|---|---|---|---|---|---|---|---|---|---|---|---|
| 1 | 1-Hexanol | 102.2 | 1.5 | 0 | 3 | 19.6 | 5 | 0.86 | 62 | 81.5[a] | <0.5[d] |
| 2 | 1-Hexanol | 102.2 | 4 | 0 | 3 | 19.6 | 5 | 2.27 | 62 | 88.6[a] | |
| 3 | 1-Hexanol | 102.2 | 4 | 1 | 3 | 19.6 | 5 | 2.27 | 62 | >99[a] | |
| 4 | 1-Hexanol | 102.2 | 1.5 | 1 | 3 | 19.6 | 5 | 0.86 | 62 | >99[a] | |
| 5 | poly(ethylene glycol) | 400 | 1.5 | 0 | 5 | 67.4 | 5 | 2.5 | 18 | >95[b] | |
| 6 | poly(ethylene glycol) | 400 | 1.5 | 0 | 5 | 67.4 | 5 | 1 | 18 | 100 | <0.5 |
| 7 | poly(ethylene glycol) | 400 | 1.5 | 0.1 | 5 | 67.4 | 5 | 1 | 18 | 100 | <0.5 |
| 8 | poly(ethylene glycol) | 400 | 1.5 | 1 | 5 | 67.4 | 5 | 1 | 18 | 100 | <0.5 |
| 9 | KRATON Liquid (R)-L-2203-2 | 3500 | 3.9 | 1 | 10 | 85.3 | 5 | 1.88 | 14 | >99[c] | |
| 10 | Trimethylol-propane | 134.2 | 2.1 | 1 | 1 | 43 | 5 | 2 | 28 | 94[c] | |
| 11 | Isosorbide | 146.1 | 2 | 2 | 2 | 20 | 5 | 1.08 | 60 | >90[c] | |
| 12 | Cholesterol | 386.4 | 2 | 1 | 5 | 20 | 5 | 1.01 | 60 | >95[c] | |
| 13 | (−)Menthol | 156.3 | 2 | 1 | 2 | 24 | 5 | 1.2 | 50 | 67[c] | |

TABLE I-continued

| Examples | Alcohol | MW, g/mol | moles phosgene/ Alcohol | moles TEA/ Alcohol | Alcohol soln wt % | Soln feed rate (g/min) | Tube Sections | Phosgene Feed rate (gm/min) | Residence Time (sec) | % alcohol conversion to chloroformate | % conversion to carbonate |
|---|---|---|---|---|---|---|---|---|---|---|---|
| 14 | 3-Pentanol | 88.1 | 2 | 1 | 2 | 20 | 5 | 1.8 | 60 | 85[b] | |
| 15 | t-Amyl alcohol | 88.2 | 2 | 1 | 2 | 20 | 5 | 1.8 | 60 | 0[c] | |
| 16 | Allyl Alcohol | 58.1 | 2 | 1 | 2 | 10.1 | 5 | 1.37 | 119 | 50[c] | |
| 17 | Propargyl Alcohol | 56.1 | 2.1 | 1 | 1.9 | 9.7 | 5 | 1.36 | 125 | 91[c] | |
| 18 | ethylene glycol | 62.1 | 4.7 | 1 | 0.9 | 13.1 | 5 | 1.75 | 92 | 22[c] | |
| 19 | 1,6-hexanediol | 118 | 3.5 | 1 | 1 | 34 | 5 | 2 | 35 | >99[c] | |
| 20 | 1,4-butanediol | 90.1 | 2 | 1 | 1 | 33 | 5 | 1.42 | 37 | >99[c] | |

[d] detection limit for carbonates in the product chloroformate.

Examples 1-20 demonstrate that the process of the present invention, generally affords high conversion of alcohols to the corresponding chloroformates with essentially no byproduct carbonate formation. It should be noted that the experiments conducted as part of this study were not optimized in all cases. Thus it is believed that much higher yields than those shown in Table 1 are achievable for aliphatic alcohol starting materials such as allyl alcohol, ethylene glycol, menthol, and the like, by adjusting various reaction parameters which are known to those skilled in the art. Such optimization falls within the scope of the instant invention.

Example 21

Interfacial Preparation of Poly(Ethylene-Butylene)Diol/BPA Co-Polycarbonate via the Corresponding Bis-Chloroformate Into a 1 L Morton reaction flask was charged 22.8 grams (g) of bisphenol-A, 0.6 g of p-cumylphenol, 100 milliliters (mL) of methylene chloride, 100 mL of distilled water, and 200 microliters (μL) of triethylamine. The flask was equipped with a calibrated pH probe, mechanical stirrer, condenser, 25% NaOH (by weight) inlet, and tube inlet. Under stirring, the pH was initially adjusted to 10.6 and controlled throughout the reaction by pumping in caustic solution (50 wt % sodium hydroxide) to maintain the pH near 10.5. A 5% weight stock solution of KRATON Liquid (R)-L-2203-2 was prepared by dissolving 26.3 grams (g) of KRATON Liquid (R)-L-2203-2 in 500 g of methylene chloride. Triethylamine (2.19 mL) was added to this stock solution. The bischloroformate of KRATON Liquid (R)-L-2203-2 was prepared by pumping the stock solution into the reaction flask at a rate of 7.6 g/min. for 3 minutes (this corresponded to 1.14 g KRATON Liquid (R)-L-2203-2, 5% weight based on bisphenol-A) while adding phosgene at a rate of 0.86 g/min (4/1 mole ratio of phosgene per Kraton OH). Each reagent was added to the first mixing section and pumped through four additional mixing sections before reaching the batch reactor. After three minutes of charging chloroformate to the Morton flask, the Kraton stock solution flow was shut off and the phosgene flow lowered to 0.75 g/min. for 16 minutes (12 g phosgene). During this step, 25% NaOH was continuously added to maintain the reaction pH around 10.5. A final pH of 9.11 was established, requiring 49.2 g of base solution. The polymer solution was separated from the brine, washed with aqueous HCl, washed twice with water, precipitated at high shear using hot water in a blender and dried. Tg=145° C., Mw=68,500 (Polystyrene standards). Proton NMR indicated that complete incorporation of the Kraton diol as BPA/Kraton carbonate was obtained.

Example 21 demonstrates that the aliphatic chloroformate product from the flow reactor can be used in its entirety and without purification to prepare co-polycarbonates under interfacial conditions.

The invention has been described in detail with particular reference to preferred embodiments thereof, but it will be understood by those skilled in the art that variations and modifications can be effected within the spirit and scope of the invention.

What is claimed is:

1. A method of preparing an aliphatic chloroformate, said method comprising:
    (a) introducing into a flow reactor at least one aliphatic hydroxyl compound said aliphatic hydroxyl compound comprising at least one aliphatic hydroxyl group, phosgene, at least one solvent, and optionally an organic base to form a unidirectional flowing reaction mixture; and
    (b) maintaining said unidirectional flowing reaction mixture at a temperature in a range between about 0° C. and about 60° C. to produce a product stream comprising an aliphatic chloroformate,
wherein only the product stream(s) exit the flow reactor.

2. The method according to claim 1 wherein said product stream is a single product stream.

3. The method according to claim 1 wherein said temperature is in a range between about 10° C. and about 50° C.

4. The method according to claim 1 wherein said unidirectional flowing reaction mixture is substantially anhydrous.

5. The method according to claim 1 wherein said flow reactor is a tubular reactor.

6. The method according to claim 1 wherein said aliphatic chloroformate comprises at least one chloroformate selected from the group consisting of monochloroformates, bischloroformates, trischloroformates, and polychloroformates.

7. The method according to claim 6 wherein said aliphatic chloroformate is a bischloroformate.

8. The method according to claim 1 wherein said unidirectional flowing reaction mixture is characterized by a molar ratio of phosgene to the aliphatic hydroxyl groups, said ratio being in a range of from about 1.1 to 1 to about 100 to 1.

9. The method according to claim 1 wherein said unidirectional flowing reaction mixture is characterized by a molar ratio of phosgene to the aliphatic hydroxyl groups, said ratio being in a range of from about 1.1 to 1 to about 4 to 1.

10. The method according to claim 1 wherein said solvent is selected from the group consisting of aliphatic solvents, and aromatic solvents.

11. The method according to claim 1 wherein said solvent is selected from the group consisting of chlorinated aliphatic solvents.

12. The method according to claim 11 wherein said solvent is methylene chloride.

13. The method according to claim 1 wherein said organic base is selected from the group consisting of amine bases and polyamine bases.

14. The method according to claim 1 wherein said unidirectional flowing reaction mixture is characterized by a molar ratio of the organic base to the aliphatic hydroxyl groups, said ratio being in a range of from about 0.01 to 1 to about 100 to 1.

15. The method according to claim 14 wherein said unidirectional flowing reaction mixture is characterized by a molar ratio of the organic base to the aliphatic hydroxyl groups, said ratio being in a range of from about 0.01 to 1 to about 5 to 1.

16. The method according to claim 14 wherein said unidirectional flowing reaction mixture is characterized by a molar ratio of the organic base to the aliphatic hydroxyl groups, said ratio being in a range of from about 0.01 to 1 to about 1.1 to 1.

17. The method according to claim 1 wherein said aliphatic hydroxyl compound comprises structural units having formula I

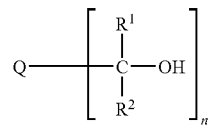

wherein $R^1$ and $R^2$ are independently at each occurrence a hydrogen atom, a $C_1$-$C_5$ aliphatic radical, a $C_3$-$C_7$ cycloaliphatic radical, an $C_3$-$C_6$ aromatic radical, or $R^1$ and $R^2$ may together form a $C_3$-$C_6$ cycloaliphatic radical; Q is a moiety having a total number of positions available for substitution and is a bond, a hydrogen atom, a $C_1$-$C_{10}$ aliphatic radical, a $C_3$-$C_6$ cycloaliphatic radical, or a $C_3$-$C_6$ aromatic radical; and n is a number from 1 to the total number of positions on Q available for substitution.

18. The method according to claim 1 wherein said aliphatic hydroxyl compound is selected from the group consisting of aliphatic mono-alcohols and aliphatic polyols.

19. The method according to claim 1 wherein said aliphatic hydroxyl compound is selected from the group consisting of polymeric aliphatic hydroxyl compounds.

\* \* \* \* \*